(12) United States Patent
Oda et al.

(10) Patent No.: US 7,326,556 B2
(45) Date of Patent: Feb. 5, 2008

(54) MICROORGANISM CAPABLE OF DEGRADING AROMATIC POLYESTER AND METHOD OF DEGRADING AROMATIC POLYESTER USING THE SAME

(75) Inventors: Kohei Oda, Izumi (JP); Yoshiharu Kimura, Omihachiman (JP); Kazumi Hiraga, Uji (JP); Yasuhito Maeda, Iwakuni (JP); Kiyotsuna Toyohara, Iwakuni (JP); Hiroyoshi Minematsu, Iwakuni (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 10/568,754

(22) PCT Filed: Aug. 19, 2004

(86) PCT No.: PCT/JP2004/012307

§ 371 (c)(1),
(2), (4) Date: Feb. 21, 2006

(87) PCT Pub. No.: WO2005/019439

PCT Pub. Date: Mar. 3, 2005

(65) Prior Publication Data

US 2006/0228792 A1    Oct. 12, 2006

(30) Foreign Application Priority Data

Aug. 22, 2003  (JP)  .............................. 2003-299338

(51) Int. Cl.
*B09B 3/00* (2006.01)
*B09C 1/10* (2006.01)
*C02F 3/34* (2006.01)
*C12N 1/20* (2006.01)

(52) U.S. Cl. .................. 435/252.2; 435/262; 435/262.5

(58) Field of Classification Search ..................... None
See application file for complete search history.

(56) References Cited

U.S. PATENT DOCUMENTS

| 5,972,042 A | 10/1999 | Barfoed et al. |
| 6,066,494 A | 5/2000 | Hsieh et al. |
| 6,376,213 B1 | 4/2002 | Oda et al. |

FOREIGN PATENT DOCUMENTS

| JP | 2000-502412 A | 2/2000 |
| JP | 2000-143868 A | 5/2000 |
| JP | 2001-502014 A | 2/2001 |
| JP | 2001-299331 A | 10/2001 |

*Primary Examiner*—David M. Naff
*Assistant Examiner*—Deborah K. Ware
(74) *Attorney, Agent, or Firm*—Sughrue Mion, Pllc.

(57) ABSTRACT

A microorganism which belongs to the genus *Rhizobium* and has the ability of degrading an aromatic polyester, and a method of degrading an aromatic polyester by using the microorganism. According to this method, the aromatic polyester can be degraded safely and relatively swiftly at a low cost.

7 Claims, 3 Drawing Sheets

F i g . 1
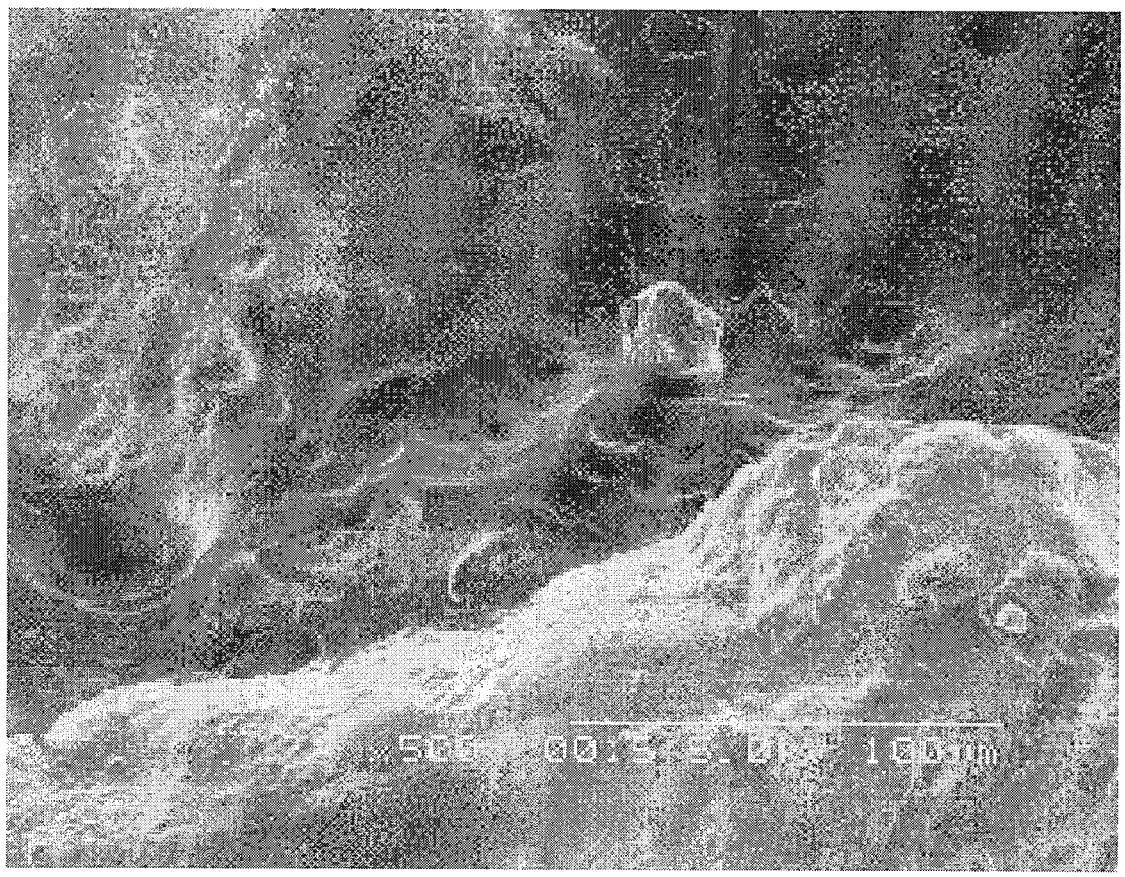

MICROORGANISM CAPABLE OF DEGRADING AROMATIC POLYESTER AND METHOD OF DEGRADING AROMATIC POLYESTER USING THE SAME

FIELD OF THE INVENTION

The present invention relates to a microorganism having the ability of degrading an aromatic polyester and to a method of degrading an aromatic polyester by using the microorganism.

DESCRIPTION OF THE PRIOR ART

Since aliphatic polyesters are degraded by ordinary soil microorganisms and known enzymes such as lipases, the research and development of the aliphatic polyesters as biodegradable polymers are now under way.

It is known that even a polyester having an aromatic component such as terephthalic acid or p-hydroxybenzoic acid can be biodegradable by a microorganism contained in soil or activated sludge, or a known enzyme when the amount of the aromatic component contained in the polyester is small or its heat resistance is extremely low. However, there are rarely known a microorganism and an enzyme for degrading an aromatic polyester comprising an aromatic component as the main ingredient such as polyethylene terephthalate (may be abbreviated as PET hereinafter). It is merely proposed that a PET fiber or PET fabric is treated with an enzyme to carry out surface modification for the improvement of its hydrophilic nature (Japanese Patent Laid-Open Publications Nos. 2000-502412 and 2001-502014 as published Japanese translations of PCT international publication). However, there are no data which definitely show the degradation of PET.

Consequently, a method of heating PET under a strong basic condition typified by a high-concentration sodium hydroxide aqueous solution is commonly used to degrade PET.

SUMMARY OF THE INVENTION

It is an object of the present invention to provide a microorganism having the ability of degrading an aromatic polyester and a method of degrading an aromatic polyester by using the microorganism.

The inventors of the present invention have conducted intensive studies on a method of degrading an aromatic polyester by the function of an organism to attain the above object and have succeeded in the isolation of a microorganism which degrades an aromatic polyester. The present invention has been accomplished based on this finding.

That is, the object of the present invention is attained by a microorganism which belongs to the genus *Rhizobium* and has the ability of degrading an aromatic polyester.

Further, the another object of the present invention is attained by a method of degrading an aromatic polyester, comprising the step of bringing a microorganism which belongs to the genus *Rhizobium* and has the ability of degrading an aromatic polyester into contact with an aromatic polyester.

According to the present invention, by using a microorganism having the ability of degrading an aromatic polyester, for example, a microorganism having the ability of degrading specifically, an aromatic polyester can be degraded under mild conditions safely and relatively swiftly at a low cost.

BRIEF DESCRIPTION OF THE DRAWINGS

FIG. 1 is a photo of *Rhizobium* sp. OKH-03 taken by a scanning electron microscope (SEM-2400 of Hitachi, Ltd.) (magnification of 20,000×);

DETAILED DESCRIPTION OF THE PREFERRED EMBODIMENT

Figure 2:
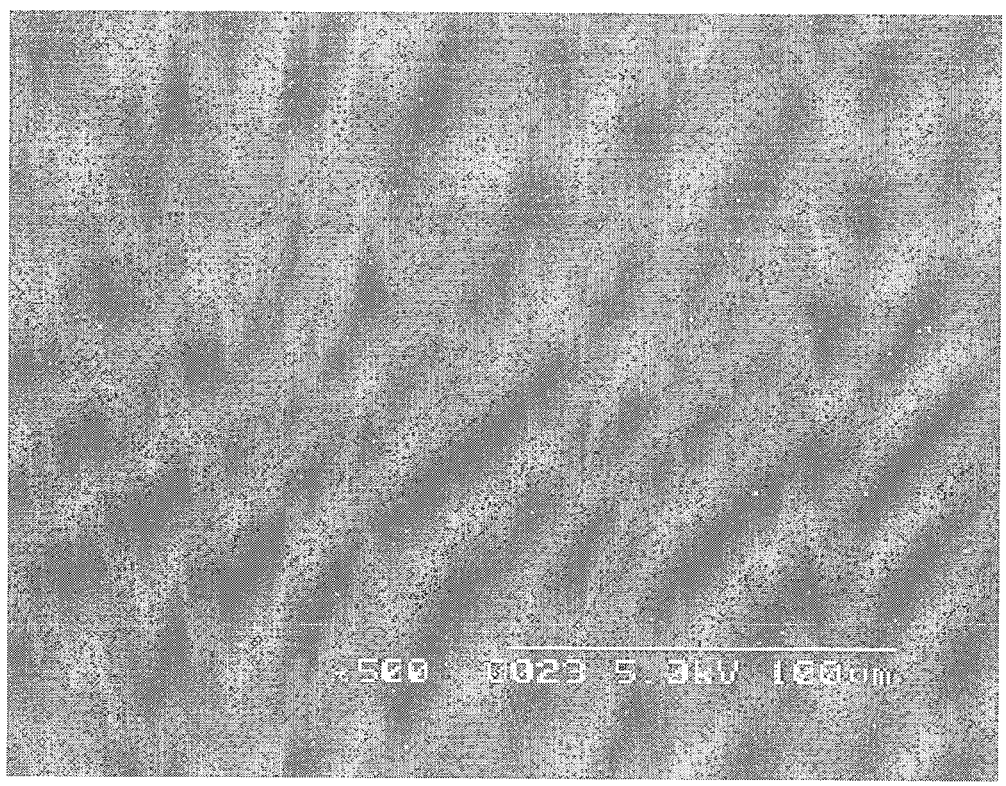
FIG. 2 is a photo of the surface of a PET film finally obtained by the operation of Example 1 taken by a scanning electron microscope (SEM-2400 of Hitachi, Ltd.) (magnification of 500×)

The present invention will be described in detail hereinunder.

In the present invention, the aromatic polyester may be a polyester which comprises 50 wt % or more of an aromatic component such as ethylene terephthalate as a recurring unit. Particularly preferably, it comprises 95 wt % or more of the ethylene terephthalate recurring unit. As for components which may be copolymerized, dicarboxylic components other than terephthalic acid are for example aromatic dicarboxylic acids and derivatives thereof such as phthalic acid, isophthalic acid, diphenyldicarboxylic acid, diphenoxyethane dicarboxylic acid and 2,6-naphthalenedicarboxylic acid, and aliphatic dicarboxylic acids and derivatives thereof such as succinic acid, adipic acid, azelaic acid, sebacic acid and decanedicarboxylic acid.

Diol components other than ethylene glycol are for example diethylene glycol, trimethylene glycol, tetramethylene glycol, propylene glycol, pentamethylene glycol, hexamethylene glycol and decamethylene glycol.

The aromatic polyester may have any shapes such as fibrous, film-like, massive or mixture thereof.

Although any microorganism is acceptable as the microorganism of the present invention if it belongs to the genus *Rhizobium* and has the ability of degrading an aromatic polyester, it is particularly preferably *Rhizobium* sp. OKH-03 (strain deposition No. FERM P-19483).

The above strain has been newly isolated from soil in Japan by the inventors and has the following mycologic properties. An SEM photo of the strain (rod-shaped bacteria) is shown in FIG. 1.

TABLE 1

| | | |
|---|---|---|
| Culture temperature | | 30° C |
| Cell form | | rod-shaped bacteria (0.8 × 1.5 to 2.0 μm) |
| Gram's stain | | − |
| Spore | | − |
| Maneuverability | | + |
| Attitude toward oxygen | | aerobic |
| Form of colony | | medium: Trypticase Soy Agar Culture time: 24 hours Circular All smooth ends Convex with a small height Glossy Light yellow |
| Culture temperature | 37° C. | + |
| | 45° C. | − |
| Catalase | | + |
| Oxidase | | − |
| Acid/gas productivity (glucose) | | −/− |
| O/F test (glucose) | | −/− |

The chemotaxonomic characteristics and the sequence of ribosomal DNA are shown in Sequence No. 1.

When it was collated with the Bergey's Manual of Systematic Bacteriology based on these properties, it was confirmed that it is a microorganism of the genus *Rhizobium* but not a known strain of the above genus. Therefore, it was deposited with the Patented Organism Deposition Center of Industrial Technical Research Laboratory (Chuoh No. 6, 1-1-1, Higashi, Tsukuba-shi, Ibaragi-ken, Japan) which is an independent administrative corporation as a new strain on Aug. 11, 2003 (accession No.: FERM P-19483). Since the microorganism of the genus *Rhizobium* is not pathogenic at bio safety level I, it is possible to carry out work biologically safely by using this strain.

A description is subsequently given of the method of isolating a microorganism which belongs to the genus *Rhizobium* and has the ability of degrading an aromatic polyester.

Since it is considered that the microorganism degrading an aromatic polyester is existent in soil and other places, a microorganism having the ability of degrading an aromatic polyester can be isolated by sampling and screening by known methods soil or seawater. Particularly preferably, the microorganism is sampled from aromatic polyester waste dumps and garbage cans.

As the culture medium is used a medium containing an aromatic polyester as a sole carbon source (may be referred to as "aromatic polyester culture medium" hereinafter).

Other nitrogen and mineral sources include inorganic ammonium salts such as ammonium sulfate and ammonium nitrate, metal salts such as iron sulfate, copper sulfate, zinc sulfate, manganese sulfate and magnesium sulfate, and hydrates thereof.

Examples of the culture include shaking culture and static culture. To obtain a specific microorganism from a mixture of microorganisms, shaking culture is preferred. Particularly preferably, enrichment culture which is carried out by limiting nutrition sources is used in combination with shaking culture.

A sample obtained from soil or the like is cultured on the above medium and the medium is newly added at intervals of a predetermined time to enrich useful bacteria.

The culture time is not particularly limited but preferably 1 to 2 months. An aromatic polyester contained in the enrichment culture solution is sampled to evaluate the aromatic polyester degrading activity of the microorganism. Although the evaluation method is not particularly limited, the observation of the surface through a scanning electron microscope is preferred because it is simple and highly reliable.

The above sample having the ability of degrading an aromatic polyester is suitably diluted and applied to an LE agar medium (medium prepared by adding agar to an LE medium) to form a colony which is then isolated (primary screening).

A strain having the great ability of degrading an aromatic polyester is screened from the primarily screened strains (secondary screening). That is, after the above biomass is multiplied until the logarithmic multiplication period and a large amount of the collected biomass is inoculated on an aromatic polyester medium to be cultured, strains having the ability of degrading an aromatic polyester can be obtained by confirming their ability of degrading an aromatic polyester.

When strains having the ability of degrading an aromatic polyester are used alone or in combination, the aromatic polyester can be degraded safety at a low cost.

The degradation method can be easily carried out by contacting the above microorganism and the aromatic polyester with each other.

Contact between the above microorganism and the aromatic polyester is preferably carried out by immersing the aromatic polyester to be degraded in an aqueous solution containing the above microorganism.

The aqueous solution is not particularly limited if it is a medium comprising the aromatic polyester as a sole carbon source. However, it is preferred to use an LE medium containing 0.2 wt % or less of an organic nutrition source other than the aromatic polyester and it is more preferred to use a medium prepared by adding an inorganic compound to the above LE medium. The term "LE medium" as used herein means a medium comprising extracts of lettuce and egg yolk and can be prepared by the following method. 3 g of lettuce leaves dried at 110° C. for 5 hours and 3 g of boiled egg yolk are decocted with 1 liter of ion exchange water for 10 minutes separately, cooled to room temperature and filtered with filter paper. These filtrate are mixed together to prepare the LE medium.

Examples of the inorganic compound to be added include inorganic ammonium salts such as ammonium sulfate and ammonium nitrate, metal salts such as iron sulfate, copper sulfate, zinc sulfate, manganese sulfate and magnesium sulfate, and hydrates thereof.

The temperature for contacting the microorganism and the aromatic polyester with each other is 40° C. or lower, preferably 20 to 37° C., more preferably 25 to 35° C., particularly preferably 30° C.

The pH for contacting the microorganism and the aromatic polyester with each other is preferably 6 to 9. To set pH to this range, when the aromatic polyester is immersed in the aqueous solution to be contacted with the microorganism, an inorganic acid such as hydrochloric acid or sulfuric acid, inorganic base such as sodium hydroxide or potassium oxide, or an aqueous solution thereof is added to the aqueous solution so as to adjust pH. A buffer solution such as a phosphoric acid buffer solution may also be used.

As for the most preferred conditions, the microorganism of the present invention and the aromatic polyester are contacted with each other in an LE medium having a temperature of 20 to 37° C. and a pH of 6 to 9. However, any other method may be employed if the aromatic polyester is degraded by contact with the microorganism.

It is preferred that a bio film should be formed on the surface of the aromatic polyester by adsorbing the microorganism to the aromatic polyester when the microorganism of the present invention and the aromatic polyester are contacted with each other. The term "bio film" as used herein means a laminar substance comprising the microorganism and its excretion. This substance firmly bonds the microorganism to the aromatic polyester and forms a place for degrading the aromatic polyester.

The time for contacting the microorganism of the present invention and the aromatic polyester with each other is at least 24 hours but may be set to any time according to the amount of the aromatic polyester to be degraded. When the contact time is longer than 2 weeks, the aqueous solution is desirably exchanged with a new one every 2 weeks.

The degradation of the aromatic polyester which is rarely degraded in the natural world can be carried out in a short period of time, for example, 0.5 to 4 months by the above methods. It was confirmed that carbon dioxide is formed as the degraded product,

EXAMPLES

The following examples are provided for the purpose of further illustrating the present invention but are in no way to be taken as limiting.

Example 1

A PET film measuring 1.4 cm×2.0 cm and a weight of 60.7 mg was prepared as an aromatic polyester by immersing it in a 0.1 N aqueous solution of hydrochloric acid for 3 hours and a 70 wt % aqueous solution of ethanol for 12 hours or more and drying it in a germ-free state to be sterilized. This PET film was sealed in a test tube equipped with a silicon stopper and having an inner diameter of 18 mm together with 10 ml of an aqueous solution medium having a pH of 7.0 and containing components shown in Table 2 and 1 ml of a culture solution containing *Rhizobium* sp. OKH-03 (deposition No.: FERM P-19483).

TABLE 2

| Composition of aqueous solution | composition |
|---|---|
| LE medium (Medium containing extracts of lettuce and egg yolk) | 99.6631 wt % |
| Ammonium sulfate | 0.2000 wt % |
| Disodium hydrogenphosphate + dihydrate | 0.1090 wt % |
| Potassium dihydrogenphosphate | 0.0265 wt % |
| Iron sulfate heptahydrate | 0.0010 wt % |
| Copper sulfate pentahydrate | 0.0001 wt % |
| Zinc sulfate heptahydrate | 0.0001 wt % |
| Manganese sulfate heptahydrate | 0.0001 wt % |
| Magnesium sulfate heptahydrate | 0.0001 wt % |

The test tube was shaken at 300 strokes/minute at 30° C. by using a horizontally shaking culture apparatus while an aerobic state was kept, and shaking culture was carried out for a total of 55 days while the solution in the test tube was exchanged with a new one every 2 weeks.

The PET film was taken out from the test tube and treated with ultrasonic waves in a 70 wt % ethanol aqueous solution for 20 minutes to remove the bio film composed of biomass and its excretion adhered to the surface of the film.

When this PET film was dried at room temperature under vacuum for 24 hours to measure its weight, the weight of the PET film after degradation was 56.2 mg, the weight loss was 7.4%, and the degradation rate was 0.015 mg/cm$^2$·day. It was confirmed by visual inspection after degration through an electron microscope that the surface was degraded as shown in FIG. 2.

Comparative Example 1

Figure 3:
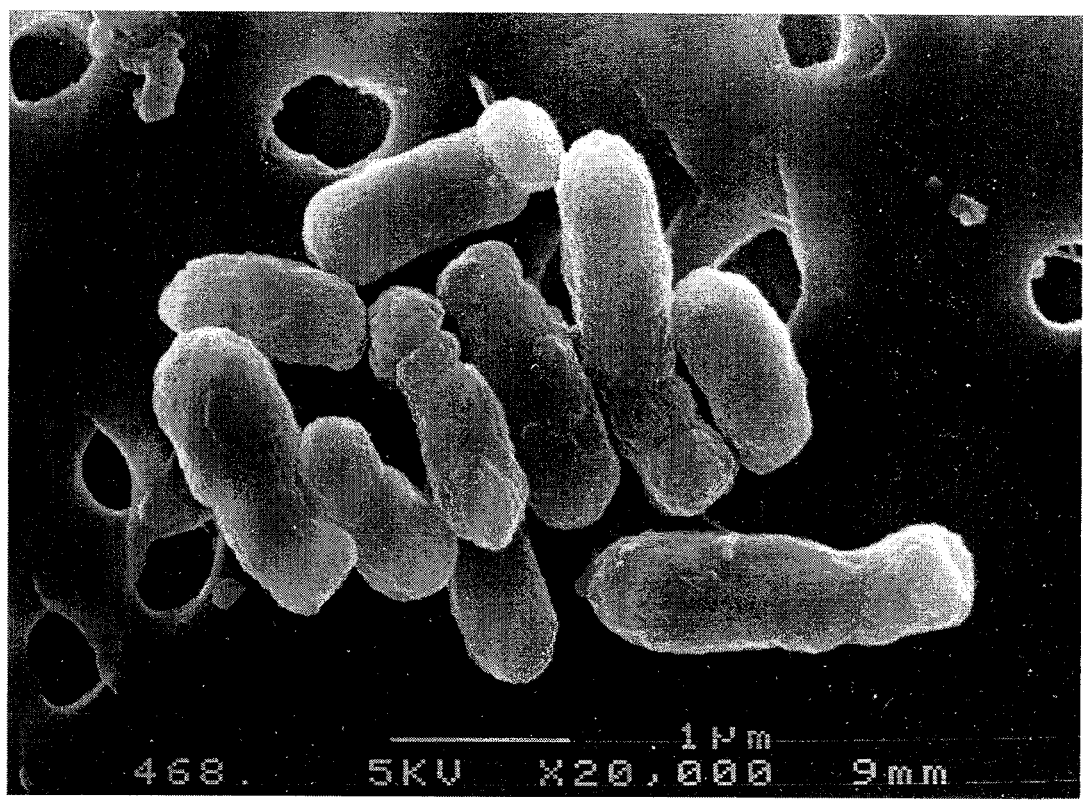
FIG. 3 is a photo of the surface of a PET film finally obtained by the operation of Comparative Example 1 taken by a scanning electron microscope (SEM-2400 of Hitachi, Ltd.) (magnification of 500×).

The operation of Example 1 was repeated except that a culture solution containing *Rhizobium* sp. OKH-03 (deposition No.: FERM P-19483) was not added. The weight of the PET film was 60.7 g, and no significant weight loss was observed. As shown in FIG. 3, it was confirmed by visual inspection through an electron microscope that the surface was not degraded.

The invention claimed is:

1. An isolated microorganism which was named *Rhizobium* sp. OKH-03 and deposited as FERM P-19483, and which has the ability of degrading an aromatic polyester.

2. A method of degrading an aromatic polyester, comprising the step of bringing the microorganism of claim 1 into contact with an aromatic polyester to degrade the aromatic polyester.

3. The method according to claim 2, wherein the aromatic polyester contains 95 wt % or more of an ethylene terephthalate recurring unit.

4. The method according to claim 2, wherein contact between the microorganism and the aromatic polyester is carried out on an LE medium which is a medium comprising extracts of lettuce and egg yolk.

5. The method according to claim 2, wherein contact between the microorganism and the aromatic polyester is carried out at 20 to 37° C.

6. The method according to claim 2, wherein contact between the microorganism and the aromatic polyester is carried out at a pH of 6 to 9.

7. The method according to claim 2, wherein contact between the microorganism and the aromatic polyester is carried out while the microorganism forms a bio film on the surface of the aromatic polyester.

* * * * *

SEQUENCE LISTING

<160> NUMBER OF SEQ ID NOS: 1

<210> SEQ ID NO 1
<211> LENGTH: 469
<212> TYPE: DNA
<213> ORGANISM: Rhizobium sp.

<400> SEQUENCE: 1

```
tggagagttt gatcctggct cagaacgaac gctggcggca ggcttaacac atgcaagtcg     60
agcgcatcgc aagatgagcg gcagacgggt gagtaacgcg tgggaatcta ccgtgcccta    120
cggaatagct ccgggaaact ggaattaata ccgtatacgc ccttcggggg aaagatttat    180
cggggtatga tgagcccgcg ttggattagc tagttggtgg ggtaaaggcc taccaaggcg    240
acgatccata gctggtctga gaggatgatc agccacattg ggactgagac acggcccaaa    300
ctcctacggg aggcagcagt ggggaatatt ggacaatggg cgcaagcctg atccagccat    360
gccgcgtgag tgatgaaggc cttaggggttg taaagctctt tcaccggtga agataatgac    420
ggtaaccgga gaagaagccc cggctaactt cgtgccagca gccgcggta                 469
```